(12) United States Patent
Moethrath et al.

(10) Patent No.: US 6,747,118 B2
(45) Date of Patent: Jun. 8, 2004

(54) STORAGE OF PHOSPHONIUM PHENOLATE CATALYSTS AND THEIR USE AS INTERESTERIFICATION CATALYSTS

(75) Inventors: Melanie Moethrath, Düsseldorf (DE); Uwe Hucks, Alpen (DE); Silke Kratschmer, Krefeld (DE); Johann Rechner, Kempen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/407,972

(22) Filed: Apr. 5, 2003

(65) Prior Publication Data

US 2003/0191016 A1 Oct. 9, 2003

(30) Foreign Application Priority Data

Apr. 9, 2002 (DE) .......................... 102 15 498

(51) Int. Cl.⁷ ................................. C08G 6/00
(52) U.S. Cl. ................ 528/196; 502/208; 528/198; 568/9
(58) Field of Search .................... 502/208; 528/196, 528/198; 568/9

(56) References Cited

U.S. PATENT DOCUMENTS

| | | | | |
|---|---|---|---|---|
| 3,442,854 | A | 5/1969 | Curtius et al. | 260/47 |
| 6,476,273 | B2 | 11/2002 | Konig et al. | 568/11 |
| 2001/0005765 | A1 | 6/2001 | Konig et al. | 568/11 |
| 2002/0177684 | A1 | 11/2002 | Kratschmer et al. | 528/196 |
| 2002/0188091 | A1 | 12/2002 | Hucks et al. | 528/196 |
| 2003/0013837 | A1 * | 1/2003 | Bunzel et al. | 528/86 |

FOREIGN PATENT DOCUMENTS

WO 01/05867 1/2001

* cited by examiner

*Primary Examiner*—Terressa Boykin
(74) *Attorney, Agent, or Firm*—Joseph C. Gil; Gary F. Matz; Aron Preis

(57) ABSTRACT

A process for preparing a melt transesterification catalyst is disclosed. The process entails (i) obtaining a phenol adduct of phosphonium phenolate in the form of crystalline solid and (ii) storing the solid phenol adduct in a closed container at relative humidity of 30 to 70 % and at temperature of −30 to 50° C. The thus prepared catalyst is suitable in the production of polycarbonate in the melt transesterification process.

4 Claims, No Drawings

STORAGE OF PHOSPHONIUM PHENOLATE CATALYSTS AND THEIR USE AS INTERESTERIFICATION CATALYSTS

FIELD OF THE INVENTION

The invention concerns transesterification catalysts and more particular phosphonium phenolate catalysts

BACKGROUND OF THE INVENTION

The production of phosphonium phenolates is known from DE 197 27 351 C1 and WO 01 46100 A. Processes for the synthesis of highly pure phosphonium phenolates, which are obtained as phenol adducts in crystalline form, are described therein. The phenol adducts of phosphonium phenolates thus obtained are used inter alia as interesterification catalysts in melt interesterification processes for the production of polycarbonate. For use in these melt interesterification processes the purity of the catalysts plays a decisive role, since impurities may lead to activity fluctuations, discoloration or secondary reactions in the interesterification process. As a rule, however, the production of phenol adducts of phosphonium phenolates is not linked either physically or in terms of apparatus to the interesterification process. That means that the catalyst has to be stored until it is used. Depending on the storage conditions, however, the purity of the catalysts and hence the quality of the end product to be obtained may deteriorate. This is commonly being compensated for by the addition of alkaline co-catalysts, such as sodium phenolate for example. The prior art contains no mention of how this problem might be overcome, however.

On the basis of the prior art the object thus arises of finding a process for the storage of phosphonium phenolates that guarantees a constant catalyst quality. Surprisingly it has now been found that storage is possible if certain parameters are maintained.

DETAILED DESCRIPTION OF THE INVENTION

The present invention therefore provides the storage of phenol adducts of phosphonium phenolates as a crystalline solid by keeping them at a certain relative humidity and certain temperatures and in closed containers. This allows storage for up to a period of five years with virtually no change in quality. The present invention therefore also provides the use of compounds stored in such a way as catalysts for the production of polycarbonate by the melt interesterification process, particularly also without additional use of alkaline co-catalysts, such as sodium phenolate for example.

Phenol adducts of phosphonium phenolates wherein the phosphonium phenolate has the formula (I) are preferably stored

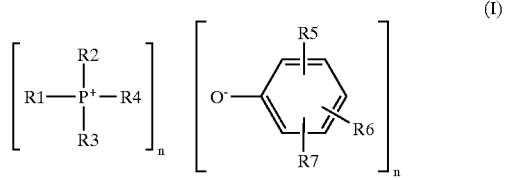

(I)

where $R_1$ to $R_4$ are the same or different and each stand for a $C_1$–$C_{12}$ alkyl, $C_5$–$C_6$ cycloalkyl, $C_7$–$C_{12}$ aryl alkyl or $C_6$–$C_{14}$ aryl radical preferably a $C_6$–$C_{14}$ aryl radical, particularly preferably for a $C_6$ aryl radical, in particular a phenyl radical, and $R_5$ to $R_7$ independently one of the others denote H, $C_1$–$C_{12}$ alkyl, $C_5$–$C_6$ cycloalkyl, $C_7$–$C_{12}$ aryl alkyl and $C_6$–$C_{14}$ aryl;

$R_5$ to $R_7$ particularly preferably denotes hydrogen n denotes 1 or 2 particularly preferably 1, and where n=2, $R_4$ denotes a $C_2$–$C_{12}$ alkylene radical.

Formula (I) most preferably stands for tetraphenyl phosphonium phenolate.

According to the invention the phenol adducts of phosphonium phenolates, preferably the phenol adducts of tetraphenyl phosphonium phenolate, are stored as a crystalline solid, preferably as a free-flowing crystalline solid.

According to the invention the phenol adducts of phosphonium phenolates, preferably the phenol adducts of tetraphenyl phosphonium phenolate, are stored in closed metal, plastic or cardboard packages. They are preferably stored in steel or plastic containers with PE liners, which are packed under air, closed and sealed under a nitrogen atmosphere. They are particularly preferably stored in steel or plastic containers with PE liners, which are packed under atmospheric conditions, closed and sealed under a nitrogen atmosphere, of a size such that they may be used as a unit for preparing metering solutions without having to be split up.

According to the invention the phenol adducts of phosphonium phenolates, preferably the phenol adducts of tetraphenyl phosphonium phenolate, are stored at temperatures of −30 to 50° C., preferably −20 to 40° C. and particularly preferably 0 to 35° C.

According to the invention the phenol adducts of phosphonium phenolates, preferably the phenol adducts of tetraphenyl phosphonium phenolate, are stored at a relative humidity of 30 to 70%, preferably 40 to 65%.

According to the invention the phenol adducts of phosphonium phenolates, preferably the phenol adducts of tetraphenyl phosphonium phenolate, may be stored for 0 to 5 years, preferably 0 to 3 years and particularly preferably 0 to 1.5 years.

The phenol adducts of phosphonium phenolates, preferably the phenol adducts of tetraphenyl phosphonium phenolate, stored according to the invention may be used in known ways as a catalyst for the production of polycarbonates (see for example U.S. Pat. No. 3,442,854). According to the melt interesterification process therein disclosed aromatic polycarbonates are produced for example from aromatic diphenols, carbonic acid diaryl esters and optionally branching agents and/or monophenols.

The phenol adducts of phosphonium phenolates, preferably the phenol adducts of tetraphenyl phosphonium phenolate, stored according to the invention are preferably used as a catalyst in the process described in DE-A 10 114 804 and in DE-A 10 119 851.

The phenol adducts of phosphonium phenolates, preferably the phenol adducts of tetraphenyl phosphonium phenolate, stored according to the invention may be used as interesterification catalysts in quantities of $10^{-1}$ mol to $10^{-8}$ mol, preferably in quantities of $10^{-3}$ mol to $10^{-7}$ mol, per mol of diphenol.

Further details of the melt interesterification process are described in the literature (see for example Hermann Schnell, Chemistry and Physics of Polycarbonates, Polymer Reviews, Vol. 9, 1964, pages 44 to 51, DE-B 1 031 512, U.S.

Pat. Nos. 3,002,272, 3,022,272, 5,340,905 and 5,399,659, DE-A 10 119 851 and DE-A 10 114 804).

The thermoplastic polycarbonates produced with the phenol adducts of phosphonium phenolates, preferably the phenol adducts of tetraphenyl phosphonium phenolate, stored according to the invention are free from solvents and have a light inherent color.

The thermoplastic polycarbonates produced with the phenol adducts of phosphonium phenolates, preferably the phenol adducts of tetraphenyl phosphonium phenolate, stored according to the invention preferably correspond to the formula (II)

(II)

wherein M denotes Ar or a defective structure A, B, C and/or D, wherein the defective structure A

does not exceed a content of 800 ppm preferably 750 ppm particularly preferably 500 ppm wherein the defective structure B

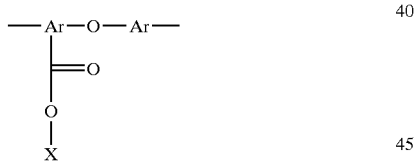

does not exceed a content of 350 ppm preferably 250 ppm particularly preferably 70 ppm wherein defective structure C

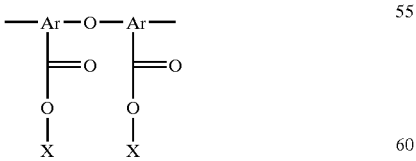

does not exceed a content of 200 ppm preferably 150 ppm particularly preferably 60 ppm wherein defective structure D

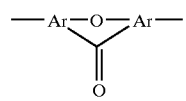

does not exceed a content of 750 ppm preferably 300 ppm particularly preferably 150 ppm wherein Y denotes H or

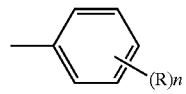

where R may be the same or different and may be H, $C_1$–$C_{20}$ alkyl, $C_6H_5$ and $C(CH_3)_2C_6H_5$, and n stands for 0, 1 or 2, whereby X denotes Y or —(MOCOO)Y, and M and Y have the meanings described above, where Ar denotes an aromatic radical with 6 to 30 C atoms, which may contain one or more aromatic nuclei, may be substituted and may contain aliphatic or cycloaliphatic radicals or alkyl aryls or heteroatoms as binding links preferably a compound represented by formula (III)

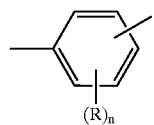
(III)

or a compound represented by formula (IV)

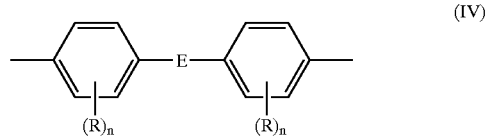
(IV)

where

E is $C_1$–$C_8$ alkylidene or $C_5$–$C_{12}$ cycloalkylidene, S, $SO_2$ or a single bond, R is a substituted or unsubstituted phenyl, methyl, propyl, ethyl, butyl, Cl or Br and n stands for 0, 1 or 2, and particularly preferably Ar represents the compounds according to the abov formula (IV).

The sum of all defective structures A to D should not exceed 1000 ppm, preferably 700 ppm, particularly preferably 550 ppm. The term ppm means ppm per weight, weight of defective structures in relation to the total weight of polycarbonate. This parameter is measured by complete hydrolysis of polycarbonate and separation of the "defective" compounds by HPLC.

EXAMPLES

The following examples are intended to illustrate the invention without however restricting it.

A $^{31}$P-NMR spectrum is recorded to identify tetraphenyl phosphonium phenolate. To this end the substance is dissolved in deuterochloroform and measured.

The content of tetraphenyl phosphonium cations and phenol/phenolate is determined using $^{13}$C-NMR. To this end a spectrum is recorded, the signals from tetraphenyl phosphonium cations and phenol/phenolate are integrated and set at 100% standardized to their molar percentages.

The water content is determined by ISO 760 (Determination of Water—Karl Fischer Method, 1$^{st}$ ed., 1978-12-01).

The color index was established as the difference in absorption at 420 nm and 700 nm in dichloromethane at a concentration of 2.4 g/50 ml and a film thickness of 10 cm.

The relative humidity was determined with the aid of a hair hygrometer.

The relative solution viscosity was determined in dichloromethane at a concentration of 5 g/l at 25° C.

The content of phenolic OH is determined by IR measurement. To this end a difference measurement of a solution of 2 g polycarbonate in 50 ml dichloromethane as compared with pure dichloromethane is measured and the absorption difference determined at 3582 cm$^{-1}$.

The content of defective structures A to D in the poly carbonate is determined by HPLC after complete saponification. To this end the polycarbonate is saponified with sodium methylate by boiling, then acidified, filtered and evaporated to dryness. The residue is dissolved in acetonitrile and detected by HPLC.

A. Production of the Phosphonium Phenolate

Tetraphenyl phosphonium phenolate is produced as a phenol adduct according to WO 01 46100 A and analysed immediately after synthesis.

376 g (4.0 mol) phenol, 800 ml deionised water, 335.44 g (0.8 mol) tetraphenyl phosphonium bromide and 640 g isobutanol are placed in a 2-1 round-bottom flask with stirrer, thermometer and dropping funnel and stirred at 20° C. to 25° C. 79 g (0.97 mol) 49% sodium hydroxide solution are added dropwise within about 5 minutes, the pH is adjusted to a range of 9.5 to 11.0. Stirring is then continued for 0.5 h at 45° C. After phase separation the lower aqueous phase is discharged and the organic phase washed three times with deionised water, the washing water as the heavy phase being discharged each time from the bottom. The organic phase is then cooled to room temperature whilst being stirred. The product crystallizes out during this process. After a crystallization time of at least 4 h the product is siphoned off. After NMR analysis for the content of phenol, isobutanol and tetraphenyl phosphonium phenolate the filtrate is returned to the reaction. The crystalline residue is rewashed with 2-propanol then dried at 100° C. in a water jet vacuum.

The results of the analysis are set out in Table 1.

TABLE 1

| Product A | |
| --- | --- |
| Parameter | Analytical value |
| TPP phenolate content | 66.3 weight % |
| Phenol content | 33.6 weight % |
| Water content | <0.06% |
| Color index | 6.6 |

B. Example

The catalyst produced according to A is packed into a steel container with PE liner under air, sealed under a nitrogen flow and stored at a relative humidity of 55% and a temperature of 20 to 25° C. for a period of one year and then analyzed. The results of the analysis are set out in Table 2.

TABLE 2

| Example | |
| --- | --- |
| Parameter | Analytical value |
| TPP phenolate content | 66.3 weight % |
| Phenol content | 33.6 weight % |
| Water content | <0.06% |
| Color index | 6.5 |

C. Comparative Examples

Comparative Example 1

The catalyst produced according to A is put into a PE container and stored for three weeks at 25° C. at a relative humidity of 90% under air in the closed PE container and then analyzed.

The results of the analysis are set out in Table 3.

TABLE 3

| Comparative example 1 | |
| --- | --- |
| Parameter | Analytical value |
| TPP phenolate content | 66.2 weight % |
| Phenol content | 33.6 weight % |
| Water content | 0.18% |
| Color index | 6.9 |

Comparative Example 2

The catalyst produced according to A is put into an open PE container under air and stored open for three weeks at 25° C. in contact with air and then analyzed. The results of the analysis are set out in Table 4.

TABLE 4

| Comparative example 2 | |
| --- | --- |
| Parameter | Analytical value |
| TPP phenolate content | 66.1 weight % |
| Phenol content | 33.7 weight % |
| Water content | 0.07% |
| Color index | 7.5 |

In $^{31}$P-NMR a peak may also be detected in the displacement region that is typical for phosphine oxides.

Comparative Example 3

The catalyst produced according to A is put into an open glass vessel, closed and stored for three weeks at 90° C. in contact with air and then analyzed.

The results of the analysis are set out in Table 5.

TABLE 5

| Comparative example 3 | |
| --- | --- |
| Parameter | Analytical value |
| TPP phenolate content | 66.3 weight % |
| Phenol content | 33.6 weight % |

TABLE 5-continued

Comparative example 3

| Parameter | Analytical value |
|---|---|
| Water content | 0.03% |
| Color index | 20.0 |

D. Application Examples

Application Examples B1 to B5

The phenol adducts of tetraphenyl phosphonium phenolates from the previous examples are used as follows for the condensation of polycarbonate.

45.66 g (0.2 mol) bisphenol A, 46.27 g (0.216 mol) diphenyl carbonate and 0.0055 g ($8 \times 10^{-4}$ mol %) of phenol adducts of tetraphenyl phosphonium phenolates from the previous examples, relative to bisphenol A, are weighed into a 500-ml three-neck flask with stirrer, internal thermometer and Vigreux column (30 cm, mirrored) with bridge. The apparatus is freed from atmospheric oxygen by application of a vacuum and rinsing with nitrogen (three times) and the mixture is melted at 150° C. and 100 mbar. The temperature is raised to 190° C. and the phenol produced is removed by distillation for 30 minutes. The temperature is then raised to 235° C. and the phenol produced removed by distillation for 10 minutes. Then within 10 minutes the vacuum is adjusted to 60 mbar and the temperature adjusted to 300° C. at the same time. After a further 10 minutes the vacuum is reduced to 0.5 mbar and stirring is continued for a further 30 minutes. The results are set out in Table 6.

TABLE 6

| Application example | Catalyst | Relative solution viscosity | % phenolic OH groups | Color index |
|---|---|---|---|---|
| B1 | A (fresh catalyst) | 1.215 | 0.033 | 0.23 |
| B2 | C. Comparative example 1 | 1.214 | 0.049 | 0.33 |
| B3 | C. Comparative example 2 | 1.232 | 0.046 | 0.36 |
| B4 | C. Comparative example 3 | 1.228 | 0.048 | 0.31 |
| B5 | B. Example | 1.220 | 0.031 | 0.21 |

Application Example B7

The quality of the phenol adduct of tetraphenyl phosphonium phenolate produced according to A and stored according to B. Example is also tested on a plant scale.

9000 kg/h of melt mixture consisting of 4600 kg diphenyl carbonate/h (21473 mol/h) and 4400 kg bisphenol A/h (19273 mol/h), with addition of 0.2628 kg of the phenol adduct of tetraphenyl phosphonium phenolate produced according to A and stored according to B. Example (0.771 mol/h), dissolved in 1.87 kg phenol/h, are pumped from a receiver through a heat exchanger, heated to 190° C. and passed through a detention column at 12000 mbar and 190° C. The average residence time is 45 minutes.

The melt is then fed through an expansion valve into a separator that is under 200 mbar. The discharging melt is reheated to 190° C. in a falling-film evaporator that is likewise under 200 mbar and collected in a receiver. After a residence time of 20 minutes the melt is pumped into the next three identically designed stages. The conditions in stages 2/3/4 are 100/75/60 mbar; 220/255/270° C. and 20/10/10 minutes. The oligomer produced has a relative viscosity of 1.068. All vapours are passed through pressure controllers into a column that is under vacuum and drawn off as condensates.

The oligomer is further polycondensed in a basket reactor at 280° C. and 7.0 mbar for a residence time of 45 minutes to form a higher-molecular oligomer. The relative viscosity is 1.134. The vapours are condensed.

The oligomer is again further polycondensed in another basket reactor at 295° C. and 1.3 mbar to a relative viscosity of 1.278. The average residence time is calculated as 130 minutes. The vapours are condensed after or in the vacuum plant.

The total residence time is 274 minutes.

The following branching agent contents are measured in the polycarbonate: structure A: 378 ppm; structure B: 7 ppm; structure C: 23 ppm; structure D: 99 ppm.

The color index of the polycarbonate is 0.19.

Application Example B8

The quality of the phenol adduct of tetraphenyl phosphonium phenolate produced according to A and stored according to C. comparative example 1 is likewise tested on a plant scale. To avoid activity fluctuations in the catalyst on this large scale small quantities of sodium phenolate must be added as co-catalyst.

10630 kg/h of melt mixture consisting of 5700 kg diphenyl carbonate/h (23667 mol/h) and 4930 kg bisphenol A/h (21595 mol/h), with addition of 0.2945 kg of the phenol adduct of tetraphenyl phosphonium phenolate produced according to A and stored according to comparative example 1 (0.864 mol/h) and 17 ppb sodium/h, added as sodium phenolate, dissolved in 2.10 kg phenol/h, are pumped from a receiver through a heat exchanger, heated to 190° C. and passed through a detention column at 12000 mbar and 190° C. The average residence time is 45 minutes.

The melt is then fed through an expansion valve into a separator that is under 200 mbar. The discharging melt is reheated to 190° C. in a falling-film evaporator that is likewise under 200 mbar and collected in a receiver. After a residence time of 20 minutes the melt is pumped into the next three identically designed stages. The conditions in stages 2/3/4 are 100/75/60 mbar; 220/255/270° C. and 20/10/10 minutes. The oligomer produced has a relative viscosity of 1.068. All vapours are passed through pressure controllers into a column that is under vacuum and drawn off as condensates.

The oligomer is condensed in a linked basket reactor at 275° C. and 7.2 mbar for a residence time of 45 minutes to form a higher-molecular oligomer. The relative viscosity is 1.134. The vapours are condensed.

The oligomer is condensed in a further basket reactor at 297° C. and 1.5 mbar to a relative viscosity of 1.293. The average residence time is calculated as 130 minutes. The vapours are condensed after or in the vacuum plant.

The total residence time is 300 minutes.

The following branching agent contents are measured in the polycarbonate: structure A: 509 ppm; structure B: 15 ppm; structure C: 35 ppm; structure D: 103 ppm.

The color index of the poly carbonate is 0.24.

As a result of the necessary addition of sodium phenolate as co-catalyst the polycarbonate produced has a higher content of branching agents. It also has a poorer inherent color than the polycarbonate produced according to application example B7.

The examples clearly demonstrate the surprising superiority of the storage according to the invention of the phenol adducts of phosphonium phenolates, preferably the phenol adducts of tetraphenyl phosphonium phenolates, and their use for the production of polycarbonates, which leads to polycarbonates that display a clearly superior color index whilst the other properties remain comparable.

On a plant scale, due to the storage according to the invention of the phenol adducts of phosphonium phenolates, preferably the phenol adducts of tetraphenyl phosphonium phenolates, the addition of an alkaline co-catalyst may surprisingly be omitted in the production of polycarbonate by the melt interesterification process.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A process for preparing a melt transesterification catalyst comprising:
    (i) obtaining a phenol adduct of phosphonium phenolate in the form of a crystalline solid and
    (ii) storing said solid in a closed container that includes a polyethylene liner, the container being sealed under nitrogen atmosphere, the containers thereafter being stored at a relative humidity of 30 to 70% and at a temperature of −30 to 50° C.,
    said melt transesterification being suitable for use in a process for the production of polycarbonate.

2. The catalyst prepared by the process of claim 1, wherein the color of and the amount of water in the catalyst does not change after being stored at a relative humidity of 30 to 70% and at a temperature of −30 to 50° C. for one year.

3. A process of using the catalyst prepared according to the process of claim 1 comprising reacting a diaryl carbonate and a dihydroxy compound in the melt and in the presence of said catalyst.

4. The process of claim 3 characterized in that the process is conducted in the absence of an alkaline co-catalyst.

* * * * *